(12) United States Patent
Abuelsaad et al.

(10) Patent No.: US 9,726,610 B2
(45) Date of Patent: Aug. 8, 2017

(54) CABLE IDENTIFICATION USING A UNIQUE CABLE SLEEVE

(71) Applicant: International Business Machines Corporation, Armonk, NY (US)

(72) Inventors: Tamer E. Abuelsaad, Somers, NY (US); John E. Moore, Brownburg, IN (US); Rajeshkumar N. Singi, Marietta, GA (US); Robert R. Wentworth, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 99 days.

(21) Appl. No.: 14/685,680

(22) Filed: Apr. 14, 2015

(65) Prior Publication Data

US 2015/0219563 A1   Aug. 6, 2015

Related U.S. Application Data

(62) Division of application No. 13/307,237, filed on Nov. 30, 2011, now abandoned.

(51) Int. Cl.
*G01J 3/30* (2006.01)
*G01J 3/46* (2006.01)
(Continued)

(52) U.S. Cl.
CPC ............ *G01N 21/718* (2013.01); *G01B 11/02* (2013.01); *G01J 3/0264* (2013.01); *G01J 3/30* (2013.01);
(Continued)

(58) Field of Classification Search
CPC . G01B 11/02; G01J 3/0264; G01J 3/30; G01J 3/443; G01J 3/46; G01J 3/50;
(Continued)

(56) References Cited

U.S. PATENT DOCUMENTS 3,491,472 A   1/1970 Walldorf
3,590,371 A   6/1971 Shaw, Jr. et al.
(Continued)

FOREIGN PATENT DOCUMENTS

CN   1095484 A    11/1994
DE   19962756 A1   6/2001
(Continued)

OTHER PUBLICATIONS

"Cable Identifier," alibaba.com, http://www.alibaba.com/showroom/cable-identifier.html, accessed on Aug. 31, 2011, pp. 1-12.
(Continued)

*Primary Examiner* — Sunghee Y Gray
(74) *Attorney, Agent, or Firm* — L. Jeffrey Kelly

(57) ABSTRACT

A cable identification system is provided. The cable identification system includes a cable sleeve with some predetermined unique properties. The cable sleeve is adapted to receive a cable therein. The cable includes one or more electrical conductors therein. The cable identification system further includes a portable measuring device configured to detect the predetermined unique properties of the cable sleeve when positioned adjacent the cable at any point along the cable.

5 Claims, 10 Drawing Sheets

(51) Int. Cl.
  *G01B 11/06* (2006.01)
  *G01B 11/02* (2006.01)
  *G01N 21/71* (2006.01)
  *G01J 3/02* (2006.01)
  *G01J 3/443* (2006.01)
  *G02B 6/38* (2006.01)
  *G01J 3/50* (2006.01)
  *H01B 7/36* (2006.01)

(52) U.S. Cl.
  CPC ............... *G01J 3/443* (2013.01); *G01J 3/46* (2013.01); *G01J 3/50* (2013.01); *G02B 6/3895* (2013.01); *H01B 7/368* (2013.01); *G01N 2201/0221* (2013.01); *G01N 2201/06113* (2013.01)

(58) Field of Classification Search
  CPC ......... G01N 21/718; G01N 2201/0221; G01N 2201/06113; G02B 6/3895; H01B 7/368
  USPC .................................. 356/318, 402, 634, 635
  See application file for complete search history.

(56) References Cited

U.S. PATENT DOCUMENTS

| | | | |
|---|---|---|---|
| 3,710,128 A * | 1/1973 | Kubisiak | G01D 5/342 250/235 |
| 4,121,152 A | 10/1978 | Hale et al. | |
| 4,199,884 A | 4/1980 | Loof | |
| 4,378,648 A | 4/1983 | Loof et al. | |
| 4,586,610 A | 5/1986 | Gandolfo | |
| D287,118 S | 12/1986 | Skarin | |
| D301,722 S | 6/1989 | Sachs | |
| 4,916,444 A | 4/1990 | King | |
| 4,947,568 A | 8/1990 | De Barbieri | |
| 5,114,517 A | 5/1992 | Rippingale et al. | |
| 5,552,699 A | 9/1996 | Redmer | |
| 5,644,237 A | 7/1997 | Eslambolchi et al. | |
| 5,922,996 A | 7/1999 | Ryeczek | |
| 5,962,827 A | 10/1999 | Zdanys, Jr. | |
| 6,353,320 B1 | 3/2002 | Eslambolchi et al. | |
| 6,456,060 B1 | 9/2002 | Wiesemann | |
| 6,577,243 B1 | 6/2003 | Dannenmann et al. | |
| 6,596,943 B1 | 7/2003 | Ward | |
| 6,646,206 B2 | 11/2003 | Ryeczek | |
| 6,651,362 B2 | 11/2003 | Caveney | |
| 6,912,329 B1 | 6/2005 | Boggs et al. | |
| 6,957,001 B2 | 10/2005 | He | |
| 7,019,658 B1 | 3/2006 | Erickson et al. | |
| 7,030,737 B2 | 4/2006 | Dove et al. | |
| 7,049,937 B1 | 5/2006 | Zweig et al. | |
| 7,134,200 B2 | 11/2006 | Boldy | |
| 7,221,284 B2 | 5/2007 | Scherer et al. | |
| 7,324,006 B2 | 1/2008 | Godard | |
| 7,367,810 B2 | 5/2008 | Lee et al. | |
| 7,612,288 B1 | 11/2009 | Gundogan et al. | |
| 7,748,860 B2 | 7/2010 | Brunet | |
| 7,948,226 B2 | 5/2011 | Rathbun, II et al. | |
| 8,729,900 B1 | 5/2014 | Dunn et al. | |
| 2002/0126286 A1 | 9/2002 | Melnyk et al. | |
| 2003/0060243 A1 | 3/2003 | Burrus, IV | |
| 2004/0156601 A1 | 8/2004 | Koyasu et al. | |
| 2006/0055584 A1 | 3/2006 | Waite et al. | |
| 2006/0084957 A1 | 4/2006 | Delfyett et al. | |
| 2006/0086527 A1 | 4/2006 | Sterkers et al. | |
| 2006/0255788 A1 | 11/2006 | Porcu et al. | |
| 2007/0221730 A1 | 9/2007 | McReynolds et al. | |
| 2008/0198618 A1 | 8/2008 | North | |
| 2008/0240724 A1 | 10/2008 | Aguren | |
| 2009/0003374 A1 | 1/2009 | Morrissey et al. | |
| 2009/0167287 A1 | 7/2009 | Van Meijl et al. | |
| 2009/0241384 A1 | 10/2009 | Duffy | |
| 2009/0272794 A1 | 11/2009 | Lange et al. | |
| 2009/0281228 A1 | 11/2009 | Kamata et al. | |
| 2009/0306918 A1 | 12/2009 | Driscoll et al. | |
| 2010/0019755 A1 | 1/2010 | Law et al. | |
| 2010/0148747 A1 | 6/2010 | Rathbun, II et al. | |
| 2010/0224328 A1 | 9/2010 | Utaka et al. | |
| 2010/0230260 A1 | 9/2010 | Bilder | |
| 2011/0112609 A1 | 5/2011 | Peterson | |
| 2011/0141943 A1 | 6/2011 | Shifris et al. | |
| 2011/0219610 A1 * | 9/2011 | Cornelison | G01B 11/043 29/825 |
| 2012/0206722 A1 * | 8/2012 | Grigoropoulos | G01N 21/718 356/318 |
| 2012/0313927 A1 * | 12/2012 | Curington | G06T 9/001 345/419 |
| 2013/0135616 A1 | 5/2013 | Abuelsaad et al. | |
| 2013/0137291 A1 | 5/2013 | Abuelsaad et al. | |
| 2013/0137292 A1 | 5/2013 | Abuelsaad et al. | |
| 2013/0138839 A1 | 5/2013 | Abuelsaad et al. | |

FOREIGN PATENT DOCUMENTS

| | | |
|---|---|---|
| FR | 2689299 A1 | 10/1993 |
| GB | 2449650 A | 3/2008 |
| JP | 2007265681 A | 10/2007 |
| JP | 2009001114 A | 1/2009 |

OTHER PUBLICATIONS

Persson et al., "Master's Thesis: Enhanced Multi Media Adaptor (EMMA)," Luleå University of Technology, A thesis performed at Ericsson Enterprise AB, submitted to meet the requirements for a degree in Master of Science, Dec. 2005, 69 pages.

"Cable Drum Management using RFID," http://usecases.race-networkrfid.eu/usecases/show/id/56, date accessed Sep. 23, 2011, 1 page.

"ESM 102: Communication Outdoor Cabling Standard," NSW Transport RailCorp, Engineering Standard Telecommunications, Version 2, Issued Jul. 2011, Approved and authorized by J. Bryon, pp. 1-18.

Shinma et al., "Cable Identification Method for Power Plants," Journal of Nuclear Science and Technology, vol. 48, No. 7, 2011, pp. 1102-1107.

"IN02 Embeddable RFID Wire Tag," William Frick & Company, http://www.fricknet.com/Products/SmartMark_RFID/IN02_Embeddable_RFID_Wire_Tag.html, accessed on Nov. 22, 2011, pp. 1-2.

* cited by examiner

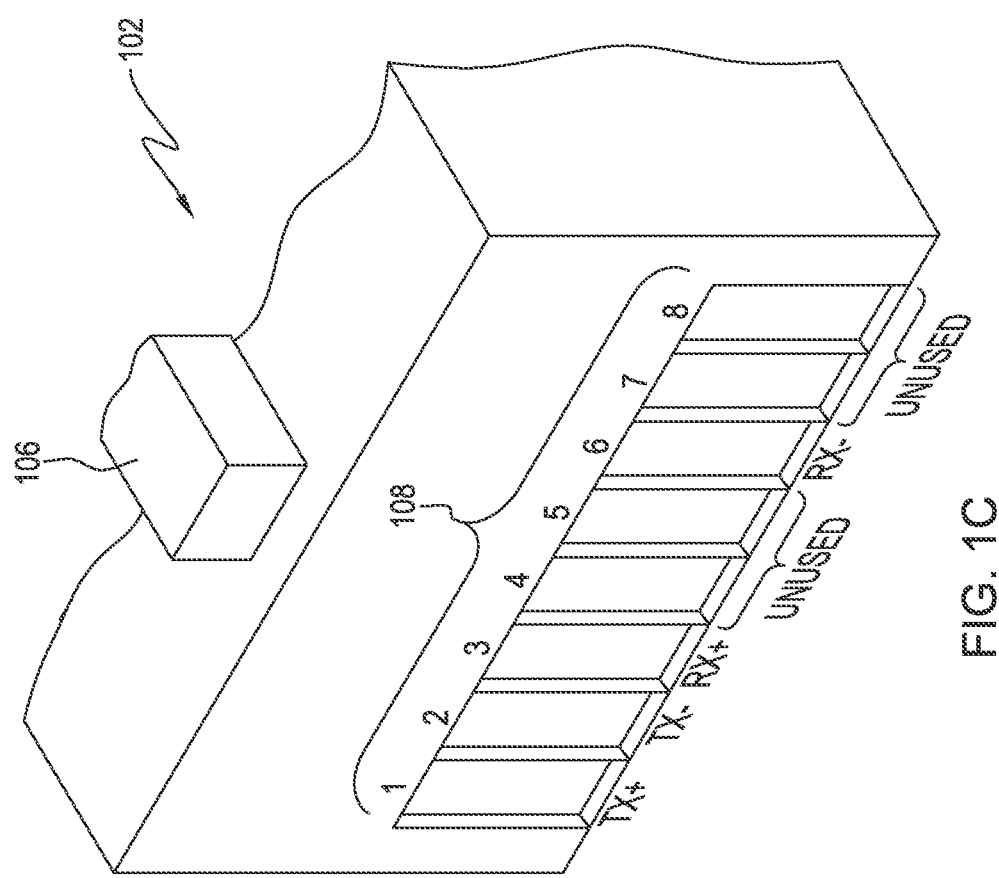

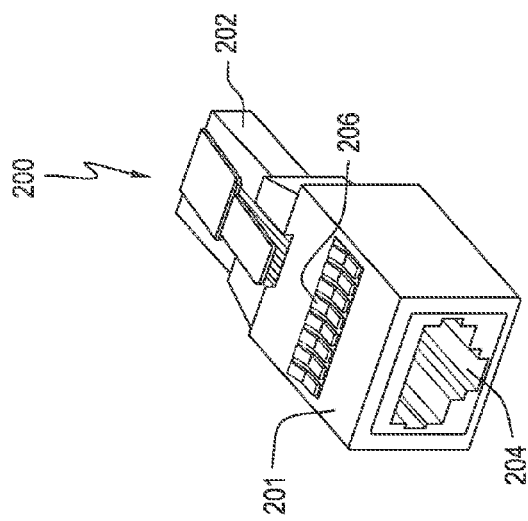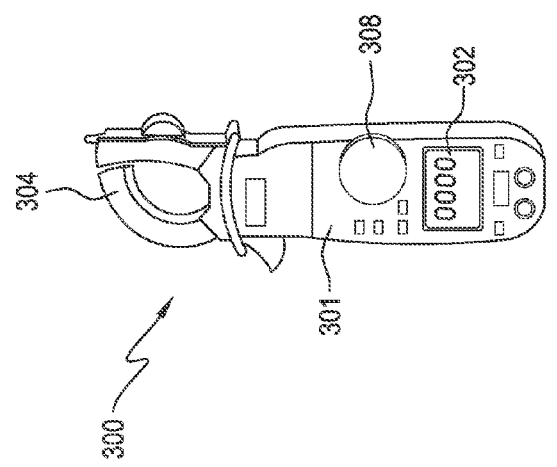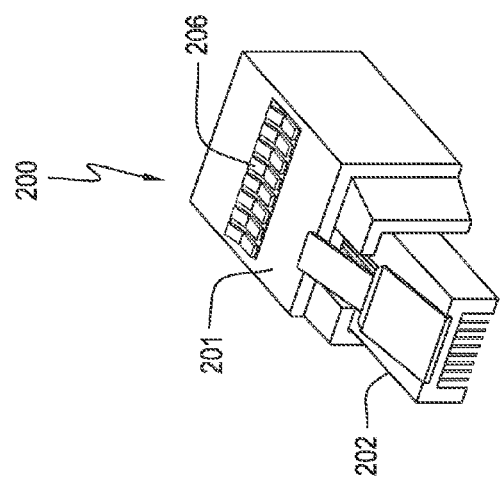

CABLE IDENTIFICATION USING A UNIQUE CABLE SLEEVE

BACKGROUND

Field of the Invention

The invention relates generally to the identification of cables. In particular the invention relates to use of a unique cable sleeve to identify a cable.

Data centers house large numbers of electronic equipment, such as computers, storage devices, and the like. Such data centers can span from a single room to multiple floors of an entire building. Servers are often stacked in rack cabinets that are placed in rows forming corridors so technicians can access the rear of each cabinet. Mainframe computers and other storage devices are often placed near the servers and can occupy spaces as large as the racks themselves.

Data centers and other networking infrastructures have an enormous number of cables connecting various electronic equipment. Even though such facilities are highly organized, the number of cables interconnecting such equipment can be overwhelming. Installing, maintaining, and tracking cables and connections to equipment can be complex. For instance, technicians need to know which cable connects to which piece of equipment. Further, if a cable becomes degraded or experiences a critical failure, then this cable needs to be readily identified.

In order to effectively manage a data center or other facility with a large amount of electronic equipment, sufficient information about cables, connections, and electronic equipment is required.

SUMMARY

In one aspect of the invention, a cable identification system includes a cable sleeve with some predetermined unique properties. The cable sleeve is adapted to receive a cable therein. The cable includes one or more electrical conductors therein. The cable identification system further includes a portable measuring device configured to detect the predetermined unique properties of the cable sleeve when positioned adjacent the cable at any point along the cable.

In another aspect of the invention, a method for identifying cables provides a cable sleeve with some predetermined unique properties. The cable sleeve is adapted to receive a cable therein. The cable includes one or more electrical conductors therein. The method for identifying cables further includes a step of inserting the cable into the cable sleeve. The method for identifying cables further includes connecting network devices at opposing ends of the cable. The method for identifying cables further includes storing an association between the predetermined unique properties of the cable sleeve and the network devices in a repository. The method for identifying cables further includes identifying the predetermined unique properties of the cable sleeve using a portable measuring device by positioning the portable measuring device adjacent the cable at any point along the cable. The method for identifying cables further includes retrieving the association between the predetermined unique properties of the cable sleeve and the network devices from the repository to identify the cable.

BRIEF DESCRIPTION OF THE SEVERAL VIEWS OF THE DRAWINGS

FIG. 1C depicts a block diagram of an exemplary RJ45 male electrical connector typically used for Ethernet cable connections;

FIGS. 2A and 2B are perspective front and rear views of a signal generator according to exemplary embodiments of the present invention;

FIG. 3 is a front view of an exemplary portable device according to embodiments of the present invention;

A more complete understanding of the present invention, as well as further features and advantages of the present invention, will be obtained by reference to the following detailed description and drawings. It is to be understood that both the foregoing general description and the following detailed description are exemplary and explanatory only, and should not be considered restrictive of the scope of the invention, as described and claimed. Further, features or variations may be provided in addition to those set forth herein. For example, embodiments of the invention may be directed to various combinations and sub-combinations of the features described in the detailed description.

DETAILED DESCRIPTION

The present invention relates to a cable identification system. More specifically, the cable identification system includes a cable sleeve with some predetermined unique properties. The cable sleeve is adapted to receive a cable therein. The cable includes one or more electrical conductors therein. The cable identification system further includes a portable measuring device configured to detect the predetermined unique properties of the cable sleeve when positioned adjacent the cable at any point along the cable. One advantage of the system presented in some embodiments of the present invention is that it does not require any special circuitry or logic to identify each cable.

Figure 1A:
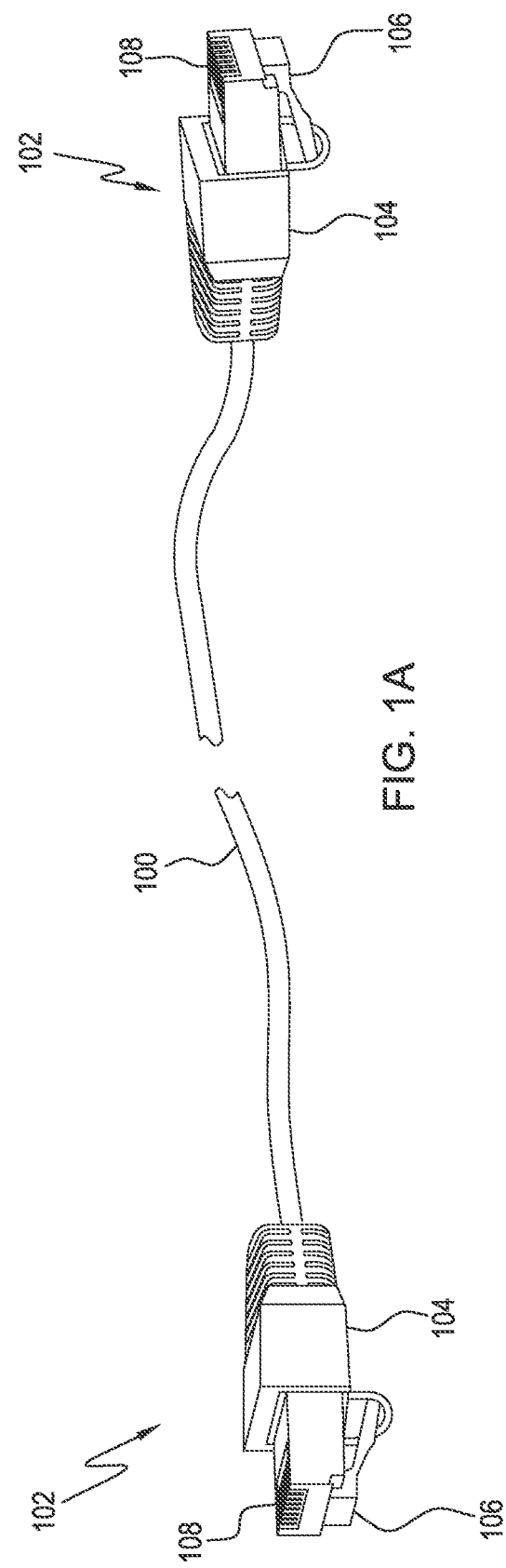
FIG. 1A is a perspective view of a networking cable according to the principles of the present invention.

With reference now to the figures, and in particular to FIG. 1A, there is depicted a cable 100, which may be utilized by the present invention. Cable 100, as used in networking applications is typically composed of a plurality of insulated conductor pairs encased in a flexible outer jacket layer. The terms "jacket" and "sleeve" are used interchangeably herein and are meant to have the same meaning. The number of wire pairs can vary depending on the application. It will be appreciated that the terms "wires" and "conductors" are used interchangeably herein. A well-known standard is the Category 5 cabling standard, which has four insulated twisted copper wires encased in an outer jacket layer, as discussed below in conjunction with FIG. 4. These are referred to as Cat5 cables. Various categories are outlined in standards, such as IEEE 802.3, IEEE802.3a, and the like, provided by the Institute of Electrical and Electronics Engineers (IEEE), located in Piscataway, N.J. Several other standards are in use and various embodiments of the instant invention anticipate the use of any of them. It should also be noted that the cable 100 may comprise coaxial, twin-axial, twisted, untwisted, shielded and unshielded pair wires, as is known in the art. Accordingly, the term "cable" as used in this description and in the appended claims will encompass all such variations.

Figure 1B:
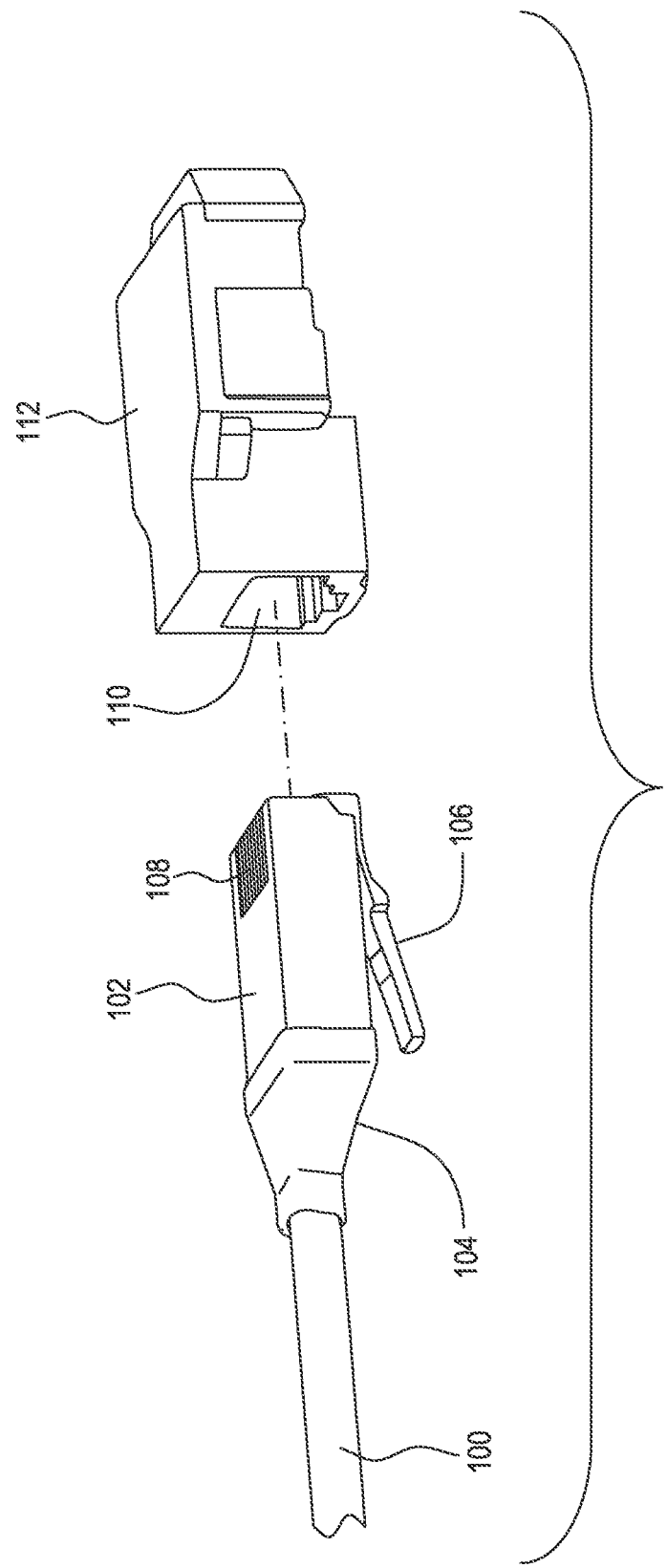
FIG. 1B is a perspective view of the networking cable of FIG. 1A illustrating one end of the networking cable mating with a mating connector.

An electrical connector 102 depicted in FIG. 1A is made up of a latch 106 and pins 108 coupled to a housing 104 on at least one end of the cable 100. Electrical connector 102 provides an electrical connection of cable 100 to various network devices depicted in FIGS. 8A and 8B. A typical electrical connector 102 is, for example, an RJ45, an eight wire connector commonly used in networking cables. Latch 106 coupled to housing 104 includes an elongated locking mechanism for engaging in a slot 110 of a mating connector 112 on a network device to effect a coupling affixation to such mating connector 112, as illustrated in FIG. 1B. It should be noted that mating connector 112 depicted in FIG. 1B may be coupled to any network device.

FIG. 1C depicts a front view of an exemplary RJ45 male connector 102 that can be used with various embodiments of the present invention. Connector 102 includes eight pins 108, each pin is coupled to a conductor in cable 100 and each pin in pins 108 is labeled 1-8 from left to right in accordance with this view. In a commonly used configuration for 10BaseT or 100BaseTX Ethernet connection, pins 1, 2, 3, and 6 are used for transmitting and receiving positive and negative voltage signals that correspond to data. Thus, in such a configuration, at least four pins and four wires in a cable remain unused.

Note that a data signal communicated over a wire in this manner is generally electrical in nature, but is different from electrical power. The data signal is different from the electrical power in that the electrical data signal has a small but sufficient voltage and/or current level to indicate a data value; whereas electrical power has voltage and/or current level that is typically larger than those of the data signal and provides sufficient energy for operating a device.

Pins 4, 5, 7, and 8 in pins 108 are depicted as unused. Those pins are coupled to four conductors in cable 100. An embodiment of the present invention employs one of the unused conductors to send a unique signal for cable identification purposes, as discussed further below. Note that this representation of an RJ45 connector in FIG. 1C and the specific pin usage are only shown for the simplicity of the illustration and are not intended to be limiting on the illustrative embodiments. Other connectors may be used without departing from the scope and spirit of the illustrative embodiments.

Referring to FIGS. 2A and 2B, exemplary embodiments of the present invention provide a signal generator, generally referred to by the reference number 200. As used herein, the term "signal generator" refers to an adapter capable of providing a detectable unique signal over one of the conductors in a cable that is plugged into such adapter. Signal generator 200 includes a housing 201 having a male connector 202 extending from a first side of the housing and a female connector 204 mounted to another side of housing 201. The male and female connectors 202 and 204 are electrically coupled one to the other via a plurality of wires disposed inside housing 201 in a conventional manner.

Figure 8A:
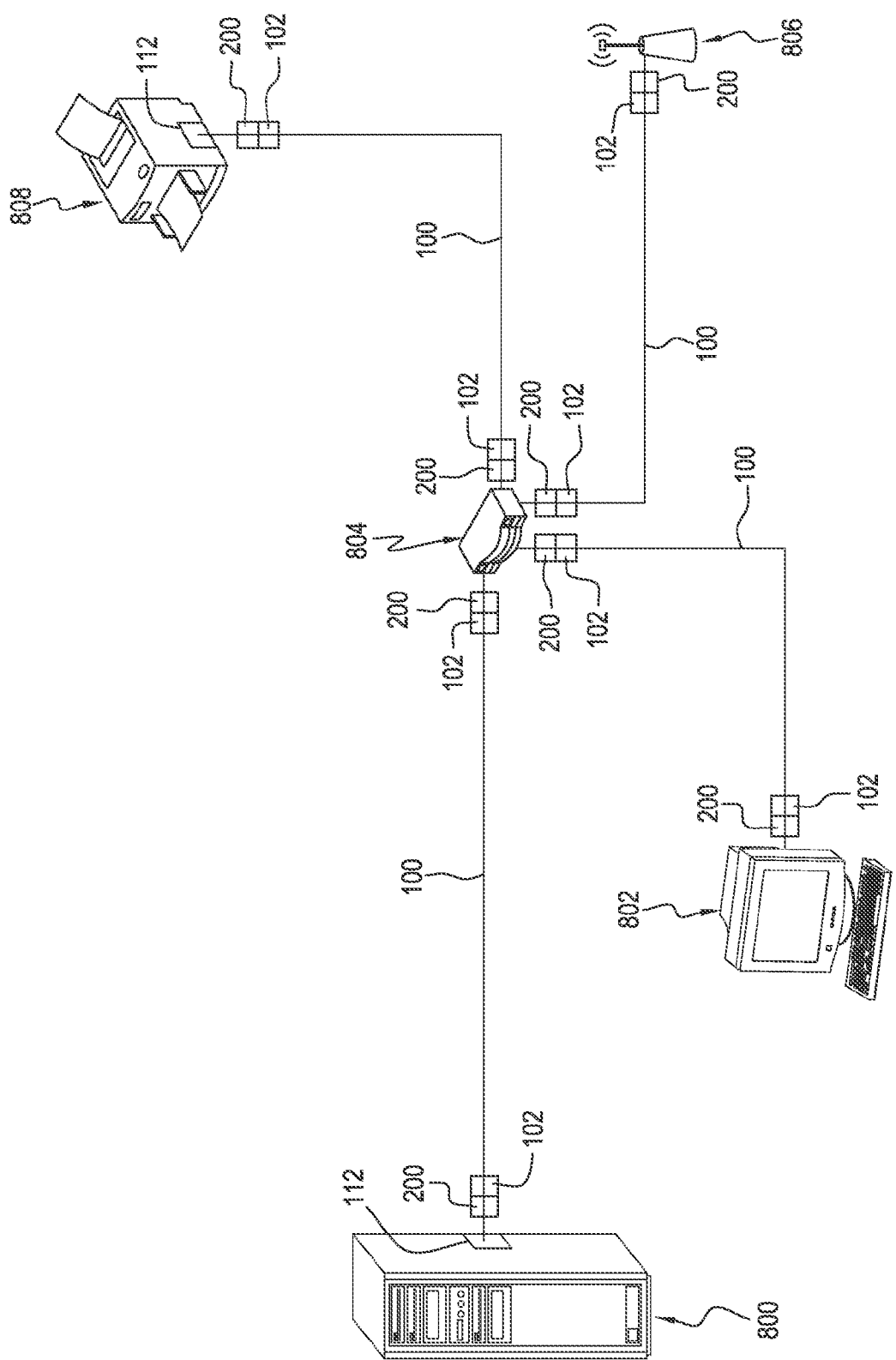
FIGS. 8A and 8B are system diagrams of network environment in which various network devices are interconnected via cables according to exemplary embodiments of the present invention.

FIG. 8A is a system diagram of network environment in which various network devices are interconnected via cables of FIG. 1A according to exemplary embodiments of the present invention. The environment includes, for example, but is not limited to, a computer server 800, client 802, router 804, wireless router 806, printer 808, and the like. These devices may be interconnected by a plurality of cables 100. The plurality of cables 100 include electrical connectors 102 at both ends for connection to a mating female connector 204 (shown in FIG. 2B) of the signal generator devices 200. In the illustrative embodiment of FIG. 8A the plurality of signal generators 200 are shown as connected between the plurality of cables 100 having male connectors 102 and various network devices 800, 804, 808 having female connectors 112. Although, not all female connectors are visible in the drawing, it is contemplated that all network devices in the network environment depicted in FIG. 8A may include such connectors. With this arrangement, signals travelling between the plurality of connectors 102 and the network devices 800, 802, 804, 806, 808 pass through signal generators 200. While signal generators 200 are coupled to both ends of cables 100 in the system illustrated in FIG. 8A, it should be understood that additional arrangements are possible. For example, signal generator 200 may be connected at one end of the cable 100, while connector 102 at the other end is connected to a mating connector 112 on the network device 800, 802, 804, 806, 808 directly. In some embodiments, when signal generator 200 is coupled at one end of cable 100, electrical connector 102 on the other end of cable 100 may be coupled to a reflector (not shown). "Reflector" is used herein to mean any device capable of reflecting an electromagnetic signal that travels through cable 100. In some embodiments, signal generator 200 may be implemented as a passive device. The term "passive device", as used herein, refers to a device that may not require any dedicated power supply source. Signal generator 200 may, for example, receive power from a network device to which it is connected. Devices connected to a data network typically contain electronic components that consume electrical power for the operation. Presently, such devices have a power source from which they derive the electrical power.

Referring back to FIGS. 2A and 2B, signal generators 200 are configured to generate and transmit a unique identification signal over each of the cables 100, as discussed below. These signals may be detected by a portable device 300, as discussed below in conjunction with FIG. 3.

Signal generator 200 may include an electrical component for generating a unique signal. In an exemplary embodiment the unique signal may comprise a unique identification number. Signal generator 200 may further include a memory unit to store the unique identification number. The unique identification number, according to an exemplary embodiment, may be transmitted through one of the unused wires in cable 100. In various embodiments, the unique identification number may be assigned to a particular signal generator 200 by a device manufacturer. The device manufacturer, in coordination with the other device manufacturers, may have policies for assigning such unique identification numbers such that each signal generator device 200 is provided with a unique identification signal in the manufacturing process. Signal generator 200 may further include the logic and control operations to select an unused conductor in cable 100 and transmit the unique signal (for example, identification number) repeatedly after a predetermined period of time. The predetermined period of time may range, for example, from about 1 second to about 5 seconds.

In a preferred embodiment at least one dual in line package (DIP) switch 206, depicted in FIGS. 2A and 2B may be used to provide a user, such as a network technician, with an opportunity to select an unused conductor among all conductors in cable 100 as a carrier of the unique ID signal. All features of DIP switches 206 are conventional and therefore are not described in detail. One of ordinary skills in the art will realize that there are many different ways of accomplishing the preferred embodiment. In an embodiment illustrated in FIGS. 2A and 2B, DIP switch assembly 206 is attached to housing 201 of signal generator 200. In this embodiment, DIP switch assembly 206 may include a slide (not shown), electrical contacts (not shown) and a plurality of switch positions. As the slide is moved linearly, the electrical contacts make and break electrical connections to a plurality of conductors in cable 100. Referring back to example illustrated in FIG. 1B, if pins 4, 5, 7, and 8 depict pins coupled to unused conductors in cable 100, network technicians may choose to use, for example, the conductor connected to pin 7 as a carrier for the unique identification signal. To accomplish this, a network technician would move the slide to position number 7 in DIP switch assembly 206. DIP switch assembly 206 may be coupled to signal generator's 200 logic configured to transmit the unique ID signal.

It should be noted that while the embodiment illustrated in FIGS. 2A and 2B depicts a signal generator as an adaptor connectable to connector 102 of cable 100, this invention is not so limited. In various embodiments, the functionality of signal generator 200 may be embedded in a network interface card (NIC) included in various network devices, such as, but not limited to, computer servers 800. The term "network interface card", as used herein, refers to a card that contains a circuit for providing network device connectivity to a network. For example, an Ethernet card is a network interface card that provides data communications capabilities over Ethernet. In an embodiment, the network interface card may be configured to select the unused conductor from the plurality of conductors and generate and transmit the unique signal over the selected conductor in cable 100. In this embodiment, the network interface card electrically coupled to any network device 800, 802, 804, 806 depicted in FIG. 8A would replace signal generator 200 connected to that device.

Referring to FIG. 3, exemplary embodiments of the present invention provide a portable device, generally referred to by the reference number 300. In various embodiments, portable device 300 may be a signal reader and could be implemented in a manner similar to existing meters for measuring electrical parameters such as current and in particular to multi-meters which include a clamp-on ammeter. Meters for measuring current, voltage and resistance or to detect electrical continuity are well known. Such meters typically include sensing circuitry as known in the art to measure one or more of these parameters. In an embodiment illustrated in FIG. 3, portable device 300 includes a palm-sized housing 301, preferably made of a suitable rigid plastic material, containing current, voltage and resistance sensing circuitry (not shown), as known in the art, and a power supply (not shown) such as, but not limited to, batteries. Housing 301 also may include a signal indicator 302 (for example, one or more light emitting diodes (LEDs)), electrically coupled to the sensing circuitry, from which the value of the identification signal can be read by the user. All features of signal reader 300 are conventional and therefore not described in detail. Housing 301 may also include a selector mechanism for switching the sensing circuitry between various sensitivity levels of current and/or voltage. In one exemplary embodiment, the selector mechanism may comprise a rotary knob 308, depicted in FIG. 3. The selector mechanism could include other functions mounted in the same housing 301. At one end of housing 301 is an inductive pick-up current clamp 304 having jaws. As is well-known, the jaws may include a conductive loop of laminated steel sheets electrically connected to the sensing circuitry and housed in plastic sheaths. When closed, the jaws form a closed magnetic inductive pick-up loop in well-known fashion. A closed loop is necessary to provide a closed electrical path to the sensing circuitry of signal reader 300. Thus, according to principles of the present invention, portable device 300, such as the signal reader described herein, is configured to detect the unique identification signal when positioned adjacent the cable at any point along the cable that needs to be identified.

Various infrastructures may be used to associate a cable having a unique signal transmitted therein with some information, such as devices connected on both ends of the cable, and to retrieve the latter given an identifier. In an embodiment a database may be used as a repository for storage of such association information. For example, once network technicians connect signal generators 200 to at least one end of cable 100 interconnecting various network devices, a record may be created in the database correlating a unique identification signal value that newly connected signal generator 200 is configured to transmit with the network devices connected at the opposing ends of the corresponding cable. At a later time, when network technicians desire to determine what cable 100 in question is connected to on both end points, they may employ portable device 300 to determine the value of the identification signal. Subsequently, network technicians may use the database to retrieve the previously created association between the identification signal value and the network devices connected to opposing ends of the cable in question.

Thus, one method of identifying cables, according to one or more embodiments of the present invention, includes using a multiconductor cable 100 having a plurality of conductors therein and having an electrical connector 102 on at least one end. At least one of the conductors in the cable remains unused for data communication purposes. The method further includes the step of coupling a signal generator 200 to electrical connector 102 on cable 100 and a mating connector 112 on a network device 800, 802, 804, 806, 808. Signal generator 200 may include the logic and control operations to select an unused conductor in cable 100 and transmit the unique identification signals repeatedly after a predetermined period of time. Alternatively, a user may select one of the unused conductors by utilizing a DIP switch 206 included in signal generator assembly 200. Subsequently, the user creates a record in a repository which associates the unique ID that will be transmitted by signal generator 200 with devices connected to the opposing ends of cable 100. At a later time, in order to determine what devices are connected by cable 100 without tracing cable 100 from end to end in both directions, a network technician may determine the unique signal value transmitted by signal generator 200 using a portable device 300 by positioning portable device 300 adjacent cable 100 at any point along cable 100. Once the unique signal value is identified, the network technician may determine electronic devices connected to opposing ends of cable 100 by retrieving a corresponding record from the central repository. Advantageously, this method enables one to identify a cable and devices interconnected by it anywhere along the length of the cable without having an access to the opposing ends of the cable.

Figure 4:
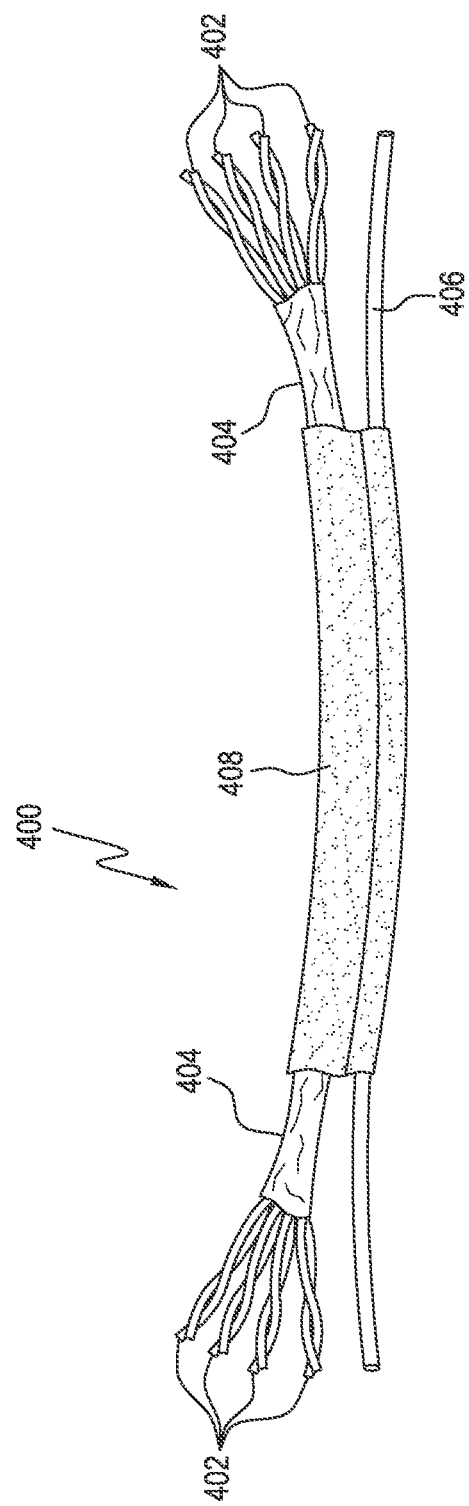
FIG. 4 is a plan view of a cable according to another embodiment of the present invention.

FIG. 4 is a plan view of a network cable according to another exemplary embodiment of the present invention.

Cable 400 depicted in FIG. 4, similarly to one or more embodiments described above, is composed of a plurality of insulated conductor pairs 402 (for example, twisted metal wire pairs) encased in a flexible outer shield conductor cover 404 and coaxially surrounded by an outer jacket layer 408. However, in this embodiment, an additional conductor 406 is added and may be positioned external to the outer surface of shield conductor 404. Furthermore, in some embodiments, additional conductor 406 may be positioned external to the outer surface of cable jacket 408 so as not to interfere with the original cable design and purpose of the specific cable type. This additional conductor 406, according to the exemplary embodiment of the present invention, may be employed as a carrier of a unique identification signal transmitted by signal generator 200 described above in conjunction with FIGS. 2A and 2B.

According to the current embodiment of the present invention, signal generator 200 may have the logic and control operations to detect additional conductor 406 in cable 400 as well as the logic to repeatedly transmit the unique identification signal described herein over additional conductor 406. Additional conductor 406 may be electrically coupled to electrical connector 102, shown in FIG. 1A. Portable device 300 may be enabled to detect and identify the unique identification signal transmitted over additional conductor 406 when positioned adjacent cable 400 at any point along cable 400 in a manner described above in conjunction with FIG. 3.

Figure 5:
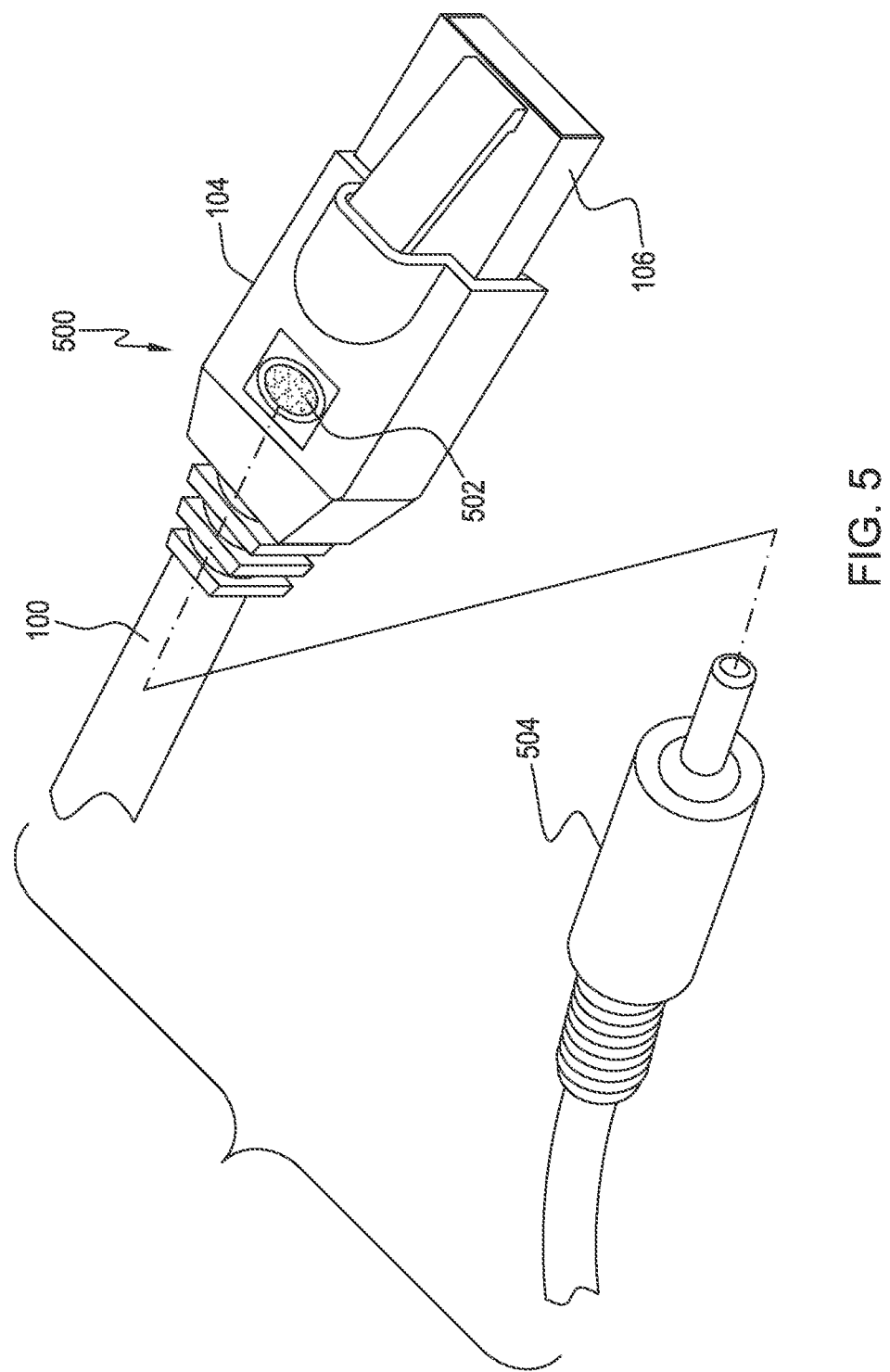
FIG. 5 is a perspective view of a modified electrical connector that may be coupled to the cable of FIG. 4 according to principles of the present invention.
Figure 6A:
FIGS. 6A-6D illustrate a plurality of cable sleeves having unique properties according to yet another embodiment of the present invention.
Figure 6B:
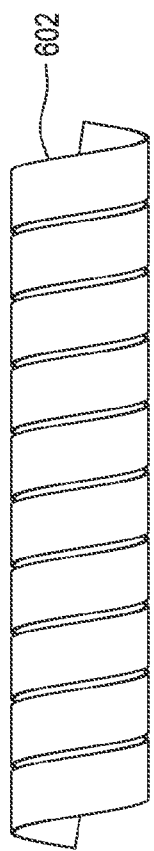
Figure 6C:
Figure 6D:
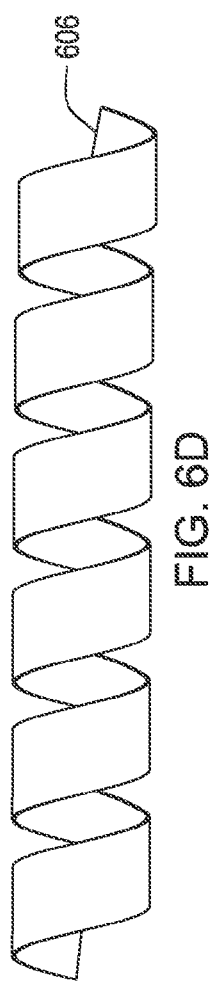

FIG. 5 is a perspective view of a modified electrical connector assembly 500 that may be coupled to the cable of FIG. 4 according to principles of the present invention. The modified electrical connector assembly 500 includes a latch 106 coupled to a housing 104 on at least one end of networking cable 400. A typical electrical connector 500 may comprise, for example, an RJ45 connector, as described above in conjunction with FIG. 1A. According to principles of the present invention, housing 104 of the typical electrical connector assembly 102 may be modified to include an inlet 502. Inlet 502 may be electrically connected to additional conductor 406 (depicted in FIG. 4). Inlet 502 may be used to supply power from an external power source to additional conductor 406 by employing, for example, a power cord 504 depicted in FIG. 5. Power cord 504 may be plugged into inlet 502 to provide power. The term "external power source", as used herein, refers to any device capable of supplying electrical energy. The external power source may comprise, for example, but not limited to, direct current (DC) or alternating current (AC) power supplies.

Note that while in some embodiments signal generator 200 may provide an electrical component configured to generate and transmit the unique ID signal over external conductor 406 in cable 100, in other embodiments, such electrical component may be included in the modified connector assembly 500. These latter embodiments contemplate that modified connector 500 depicted in FIG. 5 may connect cable 100 to mating connector 112 on a network device 800, 802, 804, 806, 808, while at the same time serving the function of signal generator 200, as described above in conjunction with FIG. 2. Thus, the current embodiment of the present invention contemplates the use of an additional conductor in a cable for identification purposes. Advantageously, the current embodiment enables one to identify a variety of different types of cables, including fiber optic cables.

FIGS. 6A-6D illustrate yet another exemplary embodiment of the present invention. Unlike the embodiments presented above, the cable identification system of FIGS. 6A-6D does not require any special circuitry or logic to identify each cable. According to this embodiment, the cable identification system comprises a plurality of cable sleeves 600, 602, 604, 606 having one or more predetermined unique property. For example, the predetermined unique property may comprise a predetermined measurable and uniquely identifiable material composition for each cable sleeve 600, 602, 604, 606. Alternately or additionally, the predetermined unique property may comprise a predetermined unique physical characteristic of each cable sleeve 600, 602, 604, 606, such as unique sicknesses, widths, color gradients and the like.

The following table provides an example of possible unique properties of cable sleeves 600, 602, 604, 606:

|  | SULPHUR | RED DIE | LEAD | POTASSIUM |
|---|---|---|---|---|
| CABLE SLEEVE 1 | 40% | 30% | 5% | 25% |
| CABLE SLEEVE 2 | 41% | 29% | 5% | 25% |
| CABLE SLEEVE 3 | 42% | 28% | 5% | 25% |

Each of cable sleeves 600, 602, 604, 606 is adapted to receive a networking cable 100 therein. In accordance with this embodiment of the present invention, cable sleeves 600, 602, 604, 606 may be sleeves that slide over each corresponding cable 100. Although, cable sleeves 600, 602, 604, 606 are depicted as having coiled shape design, they can have other suitable configurations. Other variations for cable sleeves 600, 602, 604, 606 may include tubular configuration among other configurations well-known in the art.

At some point during or after the manufacturing process, once a cable sleeve 600, 602, 604, 606 with one or more desired unique measurable properties is created a supplier may store the one or more properties in a centralized repository shared by all suppliers. Subsequently, suppliers may provide to users, such as network technicians, a plurality of cable sleeves 600, 602, 604, 606 along with the specific measurements/properties that uniquely identify each cable sleeve 600, 602, 604, 606. Network technicians may retrofit their data center's network infrastructure by inserting each cable 100 into the corresponding cable sleeve 600, 602, 604, 606 and connecting network devices to opposing ends of each cable 100. At this point, network technicians may store an association between the unique properties of each cable sleeve 600, 602, 604, 606 with the devices connected by the corresponding cable 100 in the data center's local repository, such as a database, spreadsheet, and the like.

Figure 8B:
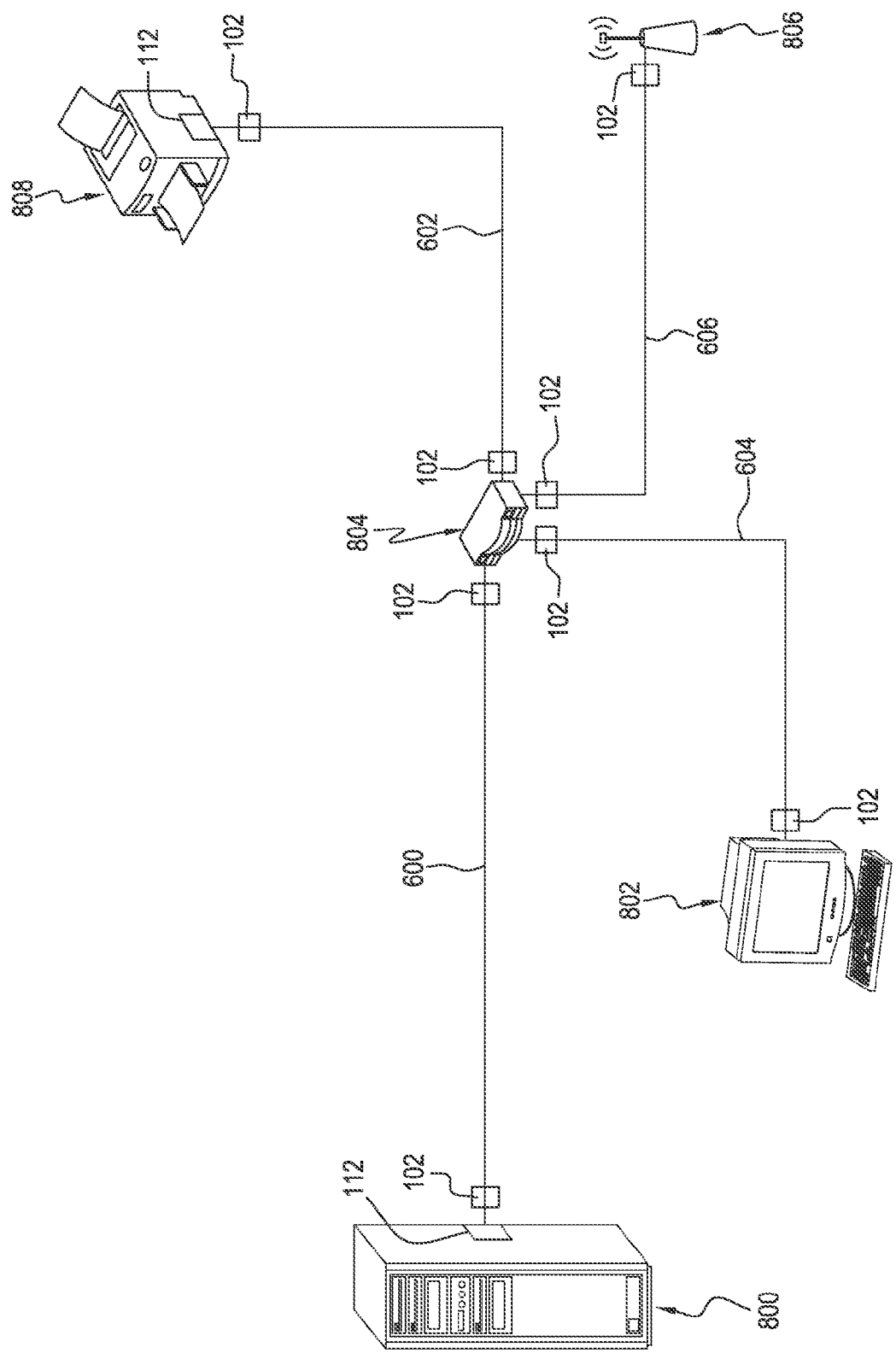

FIG. 8B is a system diagram of network environment in which various network devices 800, 802, 804, 806, 808 are interconnected via cables 100 equipped with cable sleeves 600, 602, 604, 606 of FIGS. 6A-6D according to exemplary embodiments of the present invention. The environment includes, for example, but not limited to, a computer server 800, client 802, router 804, wireless router 806, printer 808, and the like. These devices may be interconnected by a plurality of cables 100 retrofitted with a plurality of cable sleeves 600, 602, 604, 606. For example, computer server 800 may be connected to router 804 via a cable covered by the cable sleeve 600. Similarly, router 804 and printer 808 may be interconnected by the cable inserted into cable sleeve 602, as depicted in FIG. 8B. Once all network devices in a data center are interconnected, network technicians may store all associations between network devices 800, 802, 804, 806, 808 and unique properties of the corresponding cable sleeves 600, 602, 604, 606 in the local data repository. For example, one record in the local data repository may associate unique properties of cable sleeve 600 with computer server 800 and router 804 (network devices connected to opposing ends of the cable contained within cable sleeve 600). It should be noted that in the system diagram of FIG. 8B, cable 100 is used without any adapter between electrical connector 102 and mating connector 112 coupled to network devices 800, 802, 804, 806, 808. In this exemplary embodiment, when network technicians need to identify devices interconnected by a cable enclosed in, for example, cable sleeve 600, they may simply measure unique properties of cable sleeve 600 at any point along the length of the cable enclosed in cable sleeve 600. Advantageously, this method enables one to identify a cable and network devices interconnected by it anywhere along the length of the cable without having an access to the opposing ends of the cable.

Exemplary embodiments of the present invention provide a portable device capable of detecting the one or more predetermined unique properties of cable sleeves 600, 602, 604, 606. For example, portable device 300, depicted in FIG. 3, may be implemented as a portable measuring device. As will be appreciated by those skilled in the art, such measuring device may be implemented using a variety of known techniques. In one embodiment, for example, portable measuring device 300 may employ a Laser Induced Breakdown Spectroscopy (LIBS) methodology for measuring the chemical composition of cable sleeve 600, 602, 604, 606. LIBS is a type of atomic emission spectroscopy which utilizes a highly energetic laser pulse as the excitation source. Because all elements emit light when excited to sufficiently high temperatures, LIBS can detect all elements, limited only by the power of the laser as well as the sensitivity and wavelength range of the spectrograph and detector. LIBS operates by focusing a laser onto a small area at the surface of the material being examined. When the laser is discharged, it ablates a very small amount of material, in the range of approximately 1 µg, which instantaneously superheats generating a plasma plume. The ablated material dissociates (breaks down) into excited ionic and atomic species. During this time the plasma emits a continuum of radiation which does not contain any useful information about the species present. But within a very small timeframe the plasma expands at supersonic velocities and cools, at this point the characteristic atomic emission lines of the elements can be observed.

A typical portable device 300 disclosed herein that is implemented using LIBS methodology may include its own laser system, such as a Neodymium doped Yttrium Aluminum Garnet solid state laser. In addition, portable measuring device 300, in accordance with various embodiments of the present invention, may include an optical spectrometer configured to analyze chemical data from the laser induced plasma formation. The spectrometer separates the light into discrete wavelengths. Every wavelength has a unique set of spectral lines. The intensity levels for each wavelength are measured and the data is stored. This spectral data describes the chemical character and composition of the material analyzed (cable sleeve 600, 602, 604, 606). In some embodiments, portable device 300 may be preconfigured to measure only specific components within the material composition. For example, portable device 300 may be configured to measure only sulphur and magnesium levels. In other embodiments, portable device 300 may be configured to measure all chemicals that can be detected. It is contemplated, that portable measuring device 300 may be applied to various parts of cable sleeve 600, 602, 604, 606.

It should be noted that in various embodiments, portable measuring device 300 may be implemented to measure unique physical characteristics of cable sleeve 600, 602, 604, 606 such as, for example, but not limited to, a thickness and color gradients of cable sleeve 600, 602, 604, 606. In some embodiments, portable device 300 may include either volatile or non-volatile memory for storing the measured data. Furthermore, portable measuring device 300 may be adapted to compare subsequent measurements with the stored values in order to determine whether those measurements are related to the same cable sleeve.

Figure 7:
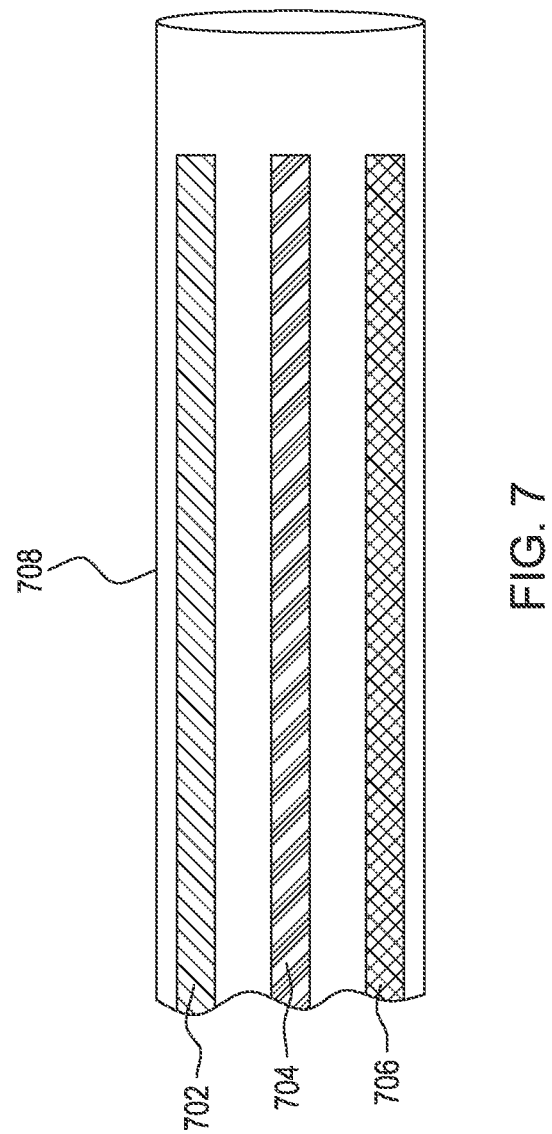
FIG. 7 is a cable sleeve according to yet another embodiment of the present invention.

FIG. 7 illustrates yet another exemplary embodiment of the present invention. In this exemplary embodiment, cable 100 may be distinguished among the plurality of cables in a data center based on the level of activity (data traffic) experienced by such cable 100. The term "level of activity" as used herein refers to average information flow of data over a predetermined period of time. Cable 100 may be connected to one or more signal generator adapters 200 depicted in FIGS. 2A and 2B. Signal generators 200 in this embodiment may be configured to include a controller operable to measure a parameter indicative of an electrical activity level of a cable 100 and generate a control signal that is related to the activity level. The controller may be of any type or any combination of circuitry. It may include discrete components, may be an integrated circuit, or a programmable logic device. In an embodiment, an activity level sensor may be coupled to the controller and adapted to measure an amount of data (data traffic) which has passed through cable 100 over a predetermined period of time. It will be understood that both the controller and the activity level sensor may comprise a pre-configured logic or circuitry or a programmable logic device. In other alternative embodiments, electrical memory devices such as electrically erasable programmable read-only memory (EEPROM), Flash EEPROM or one time programmable (OTP) PROM may be used as memory devices for storing configuration data. Configuration data may comprise, for example, various ranges of measuring units, as well as various code signals associated with various payload ranges.

Current exemplary embodiment of the present invention provides a special sleeve, such as sleeve 708 depicted in FIG. 7, adapted to contain a network cable 100 having one or more conductors 402. This special sleeve 708 may be electrically coupled to signal generator 200. In some embodiments, sleeve 708 may cover the entire cable 100, while in other embodiments sleeve 708 may cover only specific portions of the cable 100. In one embodiment, sleeve 708 may comprise the visually reacting material which would reflect a level of activity experienced by the cable 100. The visually reacting material may be electrochromic, electroluminescent or any other material which changes its appearance. Electrochromic materials change their color when electric current is passed through them. Electroluminescent materials give off light when electric current is passed through them. According to various embodiments of the present invention, sleeve 708 is electrically activatable to change an appearance in response to a signal applied directly to sleeve 708 by signal generator 200. Such change in appearance would be indicative of the level of activity in cable 100.

Note that in an embodiment, the control signal generated by signal generator 200 may take the form of a multi-bit code signal corresponding to different levels of activity within a given range. For example, code "010" generated by signal generator 200 may indicate that the level of activity is between 0 and 2 Mbps and code "111" may indicate that the level of activity is greater than 90 Mbps. It should be noted, if the predetermined period of time for which measurements are collected is 1 month, the activity level between 0 and 2 Mbps indicates the average data flow through the cable 100 over the last month.

Furthermore, each level of activity may be associated with a particular color. For instance, sleeve 708 may be adapted to change its color to blue in response to receiving code "010" and change its color to red in response to receiving code "111". In some embodiments the control signal generated by signal generator 200 may be represented by a single bit. For example, code "0" may indicate that cable 100 is not active, while code "1" may indicate that cable 100 is active. In such embodiments each binary state may be associated with a particular color as well. For instance, code "0" may be associated with black color, while code "1" may be associated with green color.

One exemplary arrangement in accordance with an embodiment of the present invention is depicted in FIG. 7. In this arrangement, sleeve 708 may have a plurality of electrically activatable segments 702, 704, 706. Each segment 702, 704, 706 may be implemented as a strip of electrochromic, electroluminescent or any other material capable of changing its appearance. Segments 702, 704, 706 may be made of the same material or different materials. With an arrangement depicted in FIG. 7 a plurality of different measurements may be represented along the length of cable 100. Each segment 702, 704, 706 may correspond to a measurement for a specific predetermined period of time. For example, segment 702 may indicate a monthly level of activity, segment 704 may indicate a daily level of activity, and segment 706 may indicate an hourly level of activity. Each segment 702, 704, 706 may have different colors at any given moment depending on a corresponding activity range. For instance, if the monthly level of activity measured by signal generator 200 is greater than 90 Mbps, it may send a control signal having a code value "111" to segment 702. Segment 702 may be adapted to change its color to red in response to receiving code value "111". Similarly, if the measured daily level of activity is between 0 and 2 Mbps, signal generator 200 may send a control signal having a code value "010" to segment 704. Segment 704 may be adapted to change its color to blue in response to receiving code value "010". It will be apparent to those skilled in the art that each of segments 702, 704 and 706 may have separate electrical connection to signal generator 200, enabling signal generator 200 to send distinct control signals to each of segments 702, 704 and 706.

Thus, one method of identifying cables, according to one embodiment of the present invention, includes using a multiconductor cable 100 having a plurality of conductors therein and having an electrical connector 102 on at least one end. The method further includes the step of placing the cable inside a special cable sleeve 708. The method further includes the step of coupling a signal generator 200 between electrical connector 102 on cable 100 and a mating connector 112 on a network device 800, 802, 804, 806, 808. Signal generator 200 may include the logic and control operations to measure and analyze at least one parameter indicative of level of activity in cable 100. The special cable sleeve 708 may have one or more segments 702, 704, 706 which are electrically activatable to change an appearance based on a control signal sent by signal generator 200 in response to the measurements indicative of level of activity in cable 100. The method further includes the step of coupling signal generator 200 to special sleeve 708. At a later time, a network technician may differentiate between the cables having various levels of activity by simply examining one or more segments 702, 704, 706 of the special cable sleeve 708 on each network cable 100.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for using one or more predetermined unique properties of a cable sleeve to identify a cable, comprising:
   providing the cable sleeve having one or more predetermined unique properties, wherein the one or more predetermined unique properties further comprise a plurality of material compositions of the cable sleeve, the cable sleeve adapted to receive the cable therein, wherein the cable comprises one or more electrical conductors therein;
   inserting the cable into the cable sleeve;
   connecting network devices at opposing ends of the cable;
   storing, in a repository, an association between the one or more predetermined unique properties of the cable sleeve and the connected network devices corresponding to the inserted cable in the cable sleeve;
   identifying the plurality of material compositions of the cable sleeve of the one or more predetermined unique properties using a portable measuring device by positioning the portable measuring device adjacent the cable at any point along the cable; and
   retrieving the association between the one or more predetermined unique properties of the cable sleeve and the network devices from the repository to identify the cable.

2. The method of claim 1, wherein the predetermined unique property further comprises a color coating gradient of the cable sleeve.

3. The method of claim 1, wherein the repository comprises a database.

4. The method of claim 1, wherein the measuring device comprises a memory unit for storing the detected properties of the cable sleeve.

5. The method of claim 1, wherein the portable measuring device utilizes the Laser Induced Breakdown Spectroscopy (LIBS) technique to identify the material composition of the cable sleeve.

* * * * *